United States Patent [19]

Gupta et al.

[11] 4,288,062

[45] Sep. 8, 1981

[54] APPARATUS FOR CONTROL AND MONITORING OF THE CARBON POTENTIAL OF AN ATMOSPHERE IN A HEAT-PROCESSING FURNACE

[75] Inventors: Bhupendra K. Gupta, Canton; Paul K. Shefsiek, Farmington, both of Mich.; Freeman W. Fraim, Lexington, Mass.

[73] Assignee: Holcroft, Livonia, Mich.

[21] Appl. No.: 65,308

[22] Filed: Aug. 9, 1979

[51] Int. Cl.³ .............................................. C21D 11/00
[52] U.S. Cl. ...................................... 266/88; 266/80; 266/81; 250/345; 73/19
[58] Field of Search .................... 148/16.5; 266/78, 80, 266/81, 87, 88; 250/343, 345; 73/19

[56] References Cited

U.S. PATENT DOCUMENTS

| | | | |
|---|---|---|---|
| 4,049,473 | 9/1977 | Davis | 148/16.5 |
| 4,108,693 | 8/1978 | L'Hermite et al. | 148/16.5 |
| 4,145,232 | 3/1979 | Solomon | 148/16.5 |
| 4,205,913 | 6/1980 | Ehrfeld | 356/72 |
| 4,208,224 | 6/1980 | Girrell | 148/16.5 |

OTHER PUBLICATIONS

"Natural Gas Heating Value Determination Using an Infrared Calorimeter", F. Fraim et al., presented AGA Transmission Conf. 5/78.
"Control of Carbon Potential in Heating Atmospheres Using a Carbon Sensor", Blumenthal et al., ASM Heat Treating Conf. Chicago, 9/75.
"Dew Point Control in Practice", O. E. Cullen, *Metal Progress* 11/54.
"Practical Experience in the Control of Heat Treatment Atmospheres Using the Oxygen Probe," N. Beach, 5th Ind. Proc. Heat. Conf., 1972.
*Metals Handbook*", 8 edition, vol. 2, American Society of Metals (1964), pp. 85-92, 113-114.
*Chemical Reaction Engineering*, Octave Levenspiel, John Wiley and Sons Inc., N. Y. 1967 pp. 205-208.

Primary Examiner—L. Dewayne Rutledge
Assistant Examiner—John P. Sheehan
Attorney, Agent, or Firm—Herbert E. Messenger; James L. Neal

[57] ABSTRACT

A system is described for precise monitoring and control of the carbon content of the atmosphere of a furnace such as a carburizer used in the heat-processing of steel parts. The disclosed apparatus includes a sampling system for withdrawing a gas sample from the atmosphere within a furnace and an analyzer for producing signals indicative of the partial pressures of at least two gaseous components such as carbon dioxide and carbon monoxide. The analyzer preferably utilizes selective absorption of narrow-band infrared radiation signals in determining these signals. A processor combines the signals indicative of partial pressures with parameters obtained from measurements of furnace temperature, and calculates carbon potential of the furnace atmosphere. The processor output is coupled with an atmosphere control which maintains desired levels of carbon potential in the atmosphere of the furnace by, for example, regulating the flow of an enriching gas to the furnace.

3 Claims, 8 Drawing Figures

APPARATUS FOR CONTROL AND MONITORING OF THE CARBON POTENTIAL OF AN ATMOSPHERE IN A HEAT-PROCESSING FURNACE

BACKGROUND OF THE INVENTION

This invention relates to monitoring and control of heat-treating processes and particularly to the control of carbon potential in the atmosphere of a carburizing furnace.

In typical carburization processes metal workpieces such as steel parts are exposed to a carbon-bearing atmosphere within a furnace. Carbon is transferred from the atmosphere to the surface of the parts and is subsequently transferred to subsurface portions by diffusion, thus hardening and strengthening the parts. To consistently achieve the desired properties in the processed parts, the content of carbon in and below the part surface must be carefully controlled. Since direct continuous measurement of the carbon concentration in the metal at the surface is not feasible, it must be inferred from the furnace atmosphere. The systems have been developed for monitoring the carbon potential of the furnace atmosphere, which is a measure of the carburizing power of the atmosphere and which defines the concentration of carbon present in the surface of a steel part in equilibrium with the furnace atmosphere.

One system for monitoring carbon potential is shown in U.S. Pat. No. 4,049,473 to R. L. Davis, II et al. This system includes a thin wire probe located in a temperature controlled chamber separate from the main furnace wherein parts are carburized. Changes in resistivity of the wire resulting from its carburization and decarburization are used to assess and control carbon potential of the main furnace atmosphere. While probes of this type are useful, they may be subject to inaccuracies due to contamination and oxidation and may also be relatively fragile.

Other known systems for determining carbon potential of a heat-treating atmosphere monitor a single parameter or component of the atmosphere. An empirical correlation between the carbon potential and the monitored parameter is then used to calculate the carbon potential. One parameter which may be monitored in a single component system is dew point of the atmosphere, which may be measured by condensing water from the atmosphere on a cool metal surface. Another parameter is carbon dioxide content which may be measured by an infrared analyzer. Alternatively, oxygen content of the atmosphere may be determined from the oxygen potential measured by a solid electrolyte oxygen concentration cell.

A major drawback of these single-parameter systems is that their use involves an assumption that non-monitored parameters remain constant during processing. If variations occur in certain non-monitored parameters, the single-parameter systems will yield inaccurate values of carbon potential as is indicated on the graphs of FIGS. 1 and 2. These figures show the effects on carbon potential of variations in temperature and carbon monoxide content which may occur in a furnace atmosphere during a heat-treating process. The effects illustrated are for a process designed to attain a carbon potential of one percent at 1700° F. FIG. 1 indicates that significant errors in carbon potential may occur in a single component carbon dioxide control system if carbon monoxide content of the furnace atmosphere deviates from the desired value of 20 percent or if temperature fluctuates from the intended setting. Similar errors, though less severe, are indicated in FIG. 2 for a single component oxygen potential control system.

Accordingly, it is an object of the present invention to provide improved apparatus for monitoring and controlling the atmosphere of a heat-processing furnace.

It is a more particular object of the invention to provide improved apparatus for monitoring the carbon potential of the atmosphere in a carburizing furnace.

It is an object of the invention to provide apparatus for determining the carbon potential in a carburizing furnace wherein the carbon potential is determined from measurements of the temperature of the furnace atmosphere and of the partial pressures of at least two gaseous components of the atmosphere.

It is also an object of the invention to provide apparatus for controlling the carbon potential of the atmosphere of a carburizing furnace.

SUMMARY OF THE INVENTION

The invention relates to a system for monitoring the carbon potential in the atmosphere of a heat-processing furnace. The system permits accurate control of the atmosphere so that desired amounts of carbon are transferred to the surfaces of steel parts during a process such as carburization.

According to the invention an apparatus for determining the carbon potential or carbon content of a steel part at equilibrium with a furnace atmosphere includes means for withdrawing a gas sample from the furnace and means such as a thermocouple for measuring the temperature of the furnace atmosphere. An analyzer is provided for receiving the gas sample and producing signals indicative of the partial pressures of selected gaseous components of the sample such as carbon dioxide and carbon monoxide. These signals and a temperature signal from the thermocouple are applied to a processor which is operable to calculate values of carbon potential of the furnace atmosphere. An atmosphere control responsive to the calculated values of carbon potential allows desired levels of carbon potential to be maintained in the furnace atmosphere by, for example, regulating the flow of an enriching gas to the furnace.

In a preferred embodiment of the invention the analyzer is an infrared analyzer comprising a source of radiation and a set of optical filters for generating narrow-band infrared radiation signals. During use of the monitoring system in the processing of steel parts in a furnace, these radiation signals are directed through a flow cell in the analyzer and are preferentially absorbed by carbon monoxide and carbon dioxide present in a sample of furnace gas passing through the flow cell. A digital processor operating on the radiation signals transmitted through the flow cell determines partial pressures of the carbon monoxide and carbon dioxide in the sample. From these partial pressures and a temperature signal, the processor calculates the activity of carbon and then the carbon potential of the furnace atmosphere at equilibrium with the steel parts. An enrichment control receives carbon potential signals from the processor and regulates the flow of natural gas to the furnace to maintain desired levels of carbon potential.

Alternate embodiments of the invention include, in addition to the infrared analyzer, an oxygen probe for measuring the oxygen content of the furnace atmosphere. According to one of these modified systems, the carbon potential or carbon content at the surface of a part at equilibrium may be determined from the carbon monoxide content of a gaseous sample as measured by the infrared analyzer and the oxygen content measured by an oxygen concentration cell extending into the furnace. In a second modified system, carbon content may be determined from the carbon monoxide and water vapor content measured by an infrared analyzer, plus the hydrogen content determined indirectly from the measured water vapor content and the oxygen content measured by the oxygen concentration cell.

DETAILED DESCRIPTION OF PREFERRED EMBODIMENTS OF THE INVENTION

Figure 1:
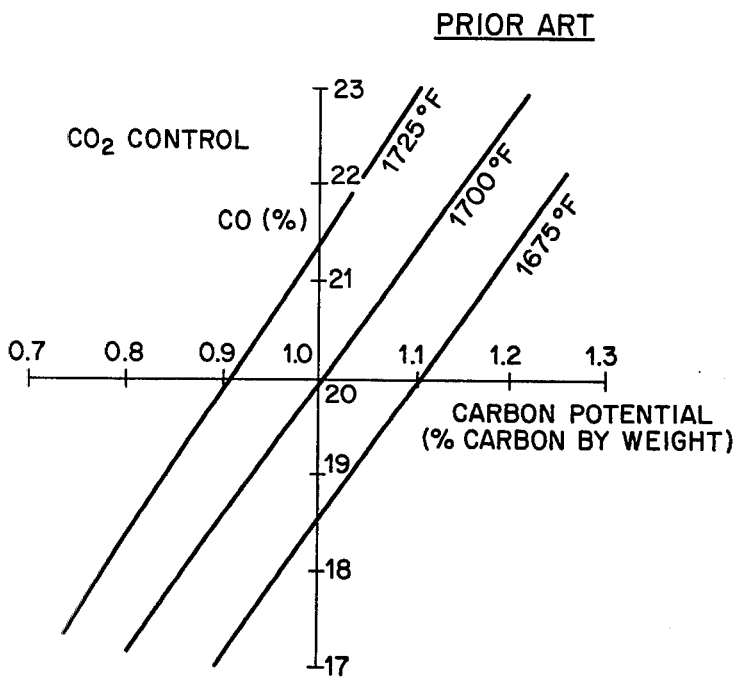
FIG. 1 is a graph showing the effect of variations in temperature and carbon monoxide content on the carbon potential of a furnace atmosphere for single component carbon dioxide control as in a prior art control system.
Figure 2:
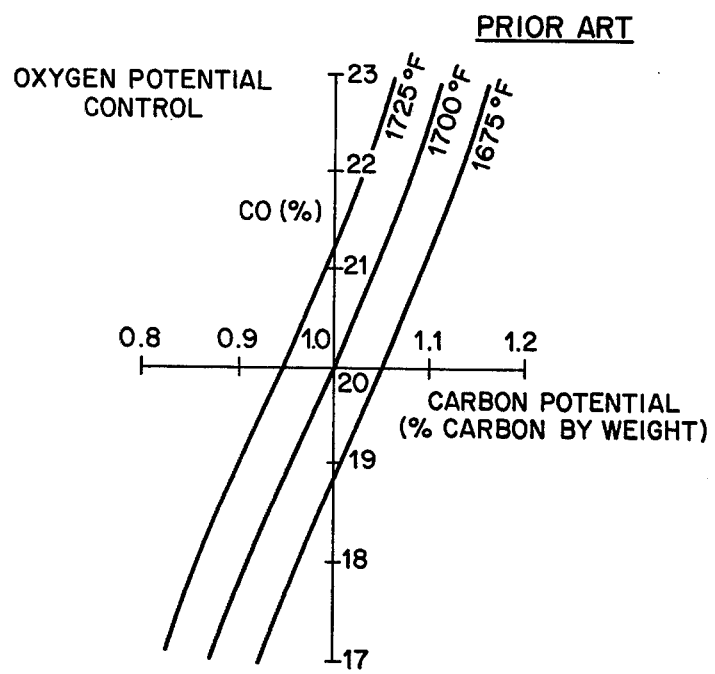
FIG. 2 is a graph showing the effect of variations in temperature and carbon monoxide content on the carbon potential of a furnace atmosphere for single component oxygen potential control as in a prior art control system.
Figure 3:
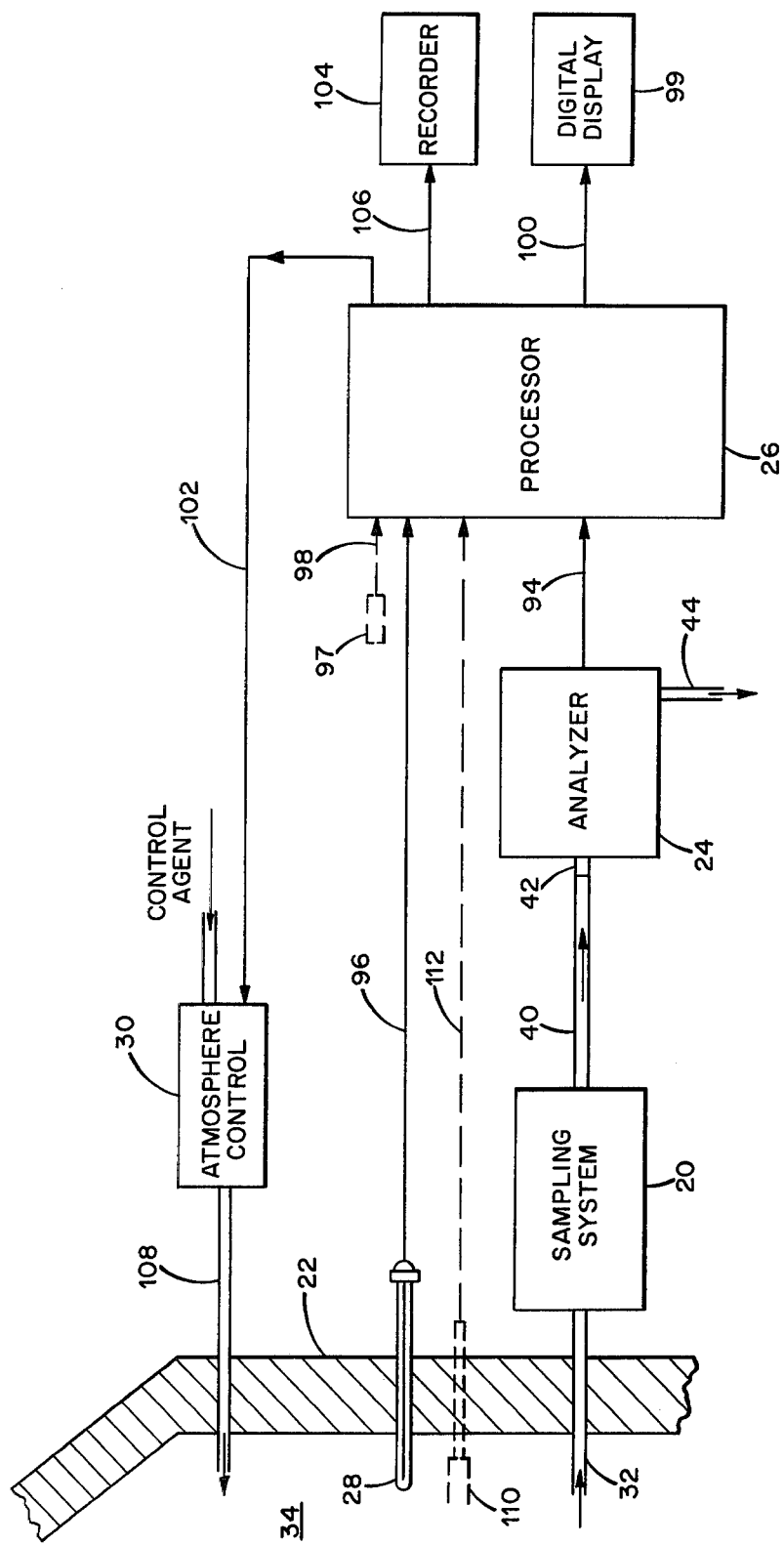
FIG. 3 is a schematic diagram, partly in block diagram form, of a preferred embodiment of the invention.

In FIG. 3 there is shown a preferred apparatus for determining the carbon potential of the atmosphere of a heat-processing furnace and for controlling the carbon potential. According to the invention, a sampling system 20 is provided for withdrawing a gas sample of the atmosphere from within a furnace 22. An analyzer 24 analyzes the sample and produces signals indicative of the partial pressures of selected gases in the sample. A processor 26 then calculates carbon potential of the furnace atmosphere using signals from the analyzer 24 and from a thermocouple 28 which measures temperature of the atmosphere within the furnace 22. Adjustment of the carbon potential of the furnace atmosphere is achieved by means of an atmosphere control 30 which regulates the flow of a control agent, typically natural gas, to the furnace 22 according to output signals received from the processor 26.

Before the structure and operation of this preferred apparatus are described in greater detail, an explanation of the principles upon which the apparatus is based will now be given.

In the carburization of steel parts in a furnace, the parts are typically exposed to an atmosphere which includes a mixture of a carrier gas and a control agent such as an enriching gas. The carrier gas may have a composition by volume of 0-30 percent carbon monoxide, 0-40 percent hydrogen, balance nitrogen, with one typical carrier gas having a nominal composition of 20 percent carbon monoxide, 40 percent hydrogen, and 40 percent nitrogen. Natural gas may be employed as the control agent, but other sources of carbon may be used. The control agent may also comprise or be diluted with air, may include ammonia for carbonitriding, and may include small amounts of carbon dioxide, water vapor, and other gases.

The concentration of carbon in the surface of a steel part undergoing heat processing in a furnace is a function of the carburizing power of the furnace atmosphere. In the following analysis it is shown that measured parameters of the furnace atmosphere can be used to calculate the activity of carbon at the surface of a part at equilibrium with the atmosphere. It is also shown that the carbon potential or concentration of carbon in the steel surface at equilibrium may be accurately determined from a relationship between carbon activity, temperature, and carbon concentration.

In a conventional furnace atmosphere, the carburizing mechanism is defined by three independent gaseous reactions:

$$CH_4 \rightleftharpoons [C] + 2H_2 \qquad (1)$$

$$2CO \rightleftharpoons [C] + CO_2 \qquad (2)$$

$$CO + H_2 \rightleftharpoons [C] + H_2O \qquad (3)$$

where [C] represents carbon in the gas phase.

The transfer of carbon from the gas phase to the steel surface is governed by the reaction

$$[C] \rightleftharpoons C \qquad (4)$$

where C represents carbon in solid solution in the steel.

The carbon activity in the gas ($a_{gi}$, where $i = 1, 2,$ or 3) for reactions (1), (2), and (3) may be expressed in the form of equilibrium relationships as follows:

$$a_{g1} = (P_{CH_4})K_1/(P_{H_2})^2 \qquad (5)$$

$$a_{g2} = (P_{CO})^2 K_2/P_{CO_2} \qquad (6)$$

$$a_{g3} = (P_{CO})(P_{H_2})K_3/P_{H_2O} \qquad (7)$$

where P = the partial pressure of the gas in the furnace atmosphere, and $K_1$, $K_2$, and $K_3$ are equilibrium constants each of which is a function of the temperature of the furnace atmosphere.

Now for an equilibrium state of one or more of the reactions (1), (2), (3) the carbon activity in the gas ($a_{gi}$) is by definition equal to the activity of carbon at the part surface ($a_s$), i.e.

$$a_{gi} = a_s \qquad (8)$$

Thus if reaction (1), (2), or (3) achieves equilibrium during heat processing, the activity of carbon at the part surface ($a_s$) can be obtained from equation (8) and the appropriate equilibrium relationship (5), (6), or (7).

Reaction (1) is known on the basis of reaction kinetics data to be extremely slow. An equilibrium state is not attained with respect to this reaction and thus it is not readily applicable for determining carbon activity or carbon potential.

Reaction (3) proceeds very quickly and its constituents attain an equilibrium state with respect to the furnace atmosphere and the part surface. Thus the activity of carbon at a part surface could be determined from equations (7) and (8) in combination with measurement of the partial pressures of CO, $H_2$, and $H_2O$ of the furnace atmosphere. However, difficulties in quickly and continuously measuring the $H_2$ content of the furnace atmosphere hinder the use of reaction (3) in the direct, real time determination of carbon potential. (As pointed out hereinafter, the $H_2$ content may be determined indirectly from measurements of other constituent gases, and thus sufficient data can be obtained to permit the use of equations (7) and (8) in calculating the activity of carbon at the part surface.)

Reaction (2) also attains an equilibrium state as will now be shown, and this reaction forms the basis for the embodiment of the invention currently preferred over all others. Now, in addition to the gaseous reactions (1), (2), and (3), the following "water-gas" reaction establishes an equilibrium between the $H_2$, $H_2O$, CO, and $CO_2$ gases in the furnace atmosphere:

$$CO + H_2O \rightleftharpoons H_2 + CO_2 \qquad (9)$$

Figure 4:
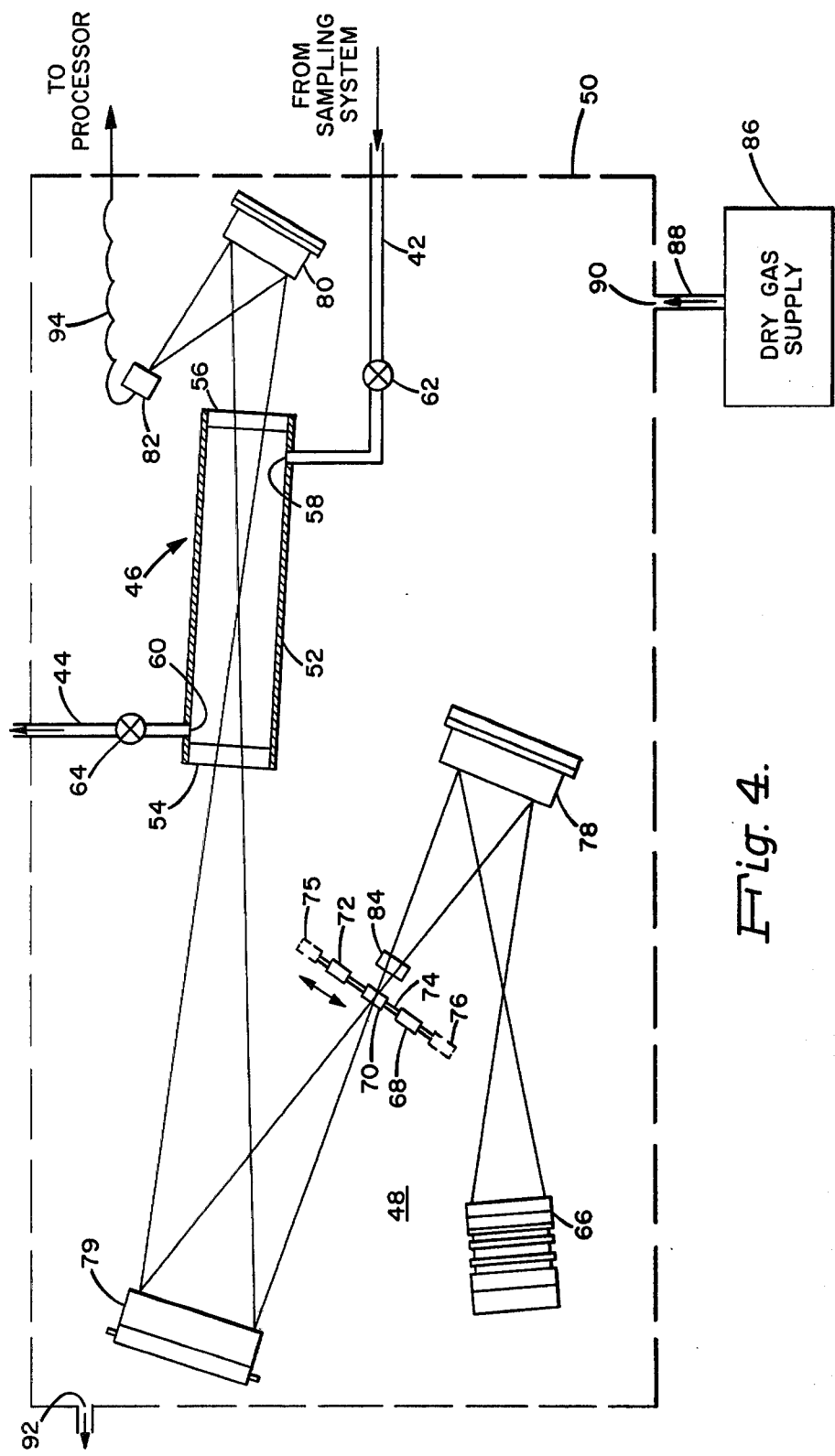
FIG. 4 is a schematic diagram, partly in block diagram form, of an infrared analyzer suitable for use in the apparatus of FIG. 3.

Since reaction (2) may be obtained by adding reactions (3) and (9), both of which achieve equilibrium, reaction (2) also attains an equilibrium with the furnace atmosphere and with the parts being carburized. Thus equations (6) and (8) may be used to directly determined carbon activity at the part surface ($a_s$) if the partial pressures of CO and $CO_2$ can be measured ($K_2$ can be obtained from temperature measurements of the furnace atmosphere). As is pointed out below in connection with a preferred embodiment of the invention, the infrared analyzer 24 shown in FIGS. 3 and 4 is uniquely suited for measuring these partial pressures.

After values of carbon activity ($a_s$) have been determined according to the above-described technique, the carbon content in the surface of a part at equilibrium may be calculated from an equation which relates carbon content to carbon activity and temperature. For austenite the form of iron normally present in steel parts undergoing carburization, an equation wwhich has analytically been found to produce accurate values of carbon content is:

$$\log a_s 32\ 4140/T - 0.920 + 6950\ (r/T) + \log (r/(l-r)) \qquad (10)$$

where

T = temperature (°R) of the part and of the furnace atmosphere, and r = atom number ratio (number of carbon atoms divided by the number of iron atoms).

Thus for each measured value of temperature of the furnace atmosphere and a value of surface carbon activity ($a_s$), the atom number ratio may be calculated from equation (10).

The carbon content of the surface of a steel part may then be readily determined from the expression $$W_C = 100 r M_C/(r M_C + M_{Fe}) \qquad (11)$$

where $W_C$ = carbon potential or percent carbon by weight at the part surface, $M_C$ = atomic weight of carbon, and $M_{Fe}$ = atomic weight of iron.

The effect on carbon concentration of the addition of alloying elements such as nickel, chromium, and cobalt to a steel part may be accounted for by adjusting the calculated activity of carbon at the part surface. One suitable factor F by which the activity $a_s$ may be multiplied to obtain an adjusted activity is defined as $$F = \Sigma_i a_i A_i \qquad (12)$$

where $A_i$ = concentration of $i^{th}$ alloy $a_i$ = interaction parameter of $i^{th}$ alloy.

Reference is again made to FIG. 3 which shows a preferred embodiment of the invention according to which the carbon potential of the atmosphere within the furnace 22 may be accurately determined and controlled.

In order to obtain a sample of gas for measurement of partial pressures of gaseous components such as carbon monoxide and carbon dioxide and to permit use thereof in the calculation of carbon activity, a sample tube 32 extends through a wall of the furnace 22 and into a carburizing chamber 34 which contains the furnace atmosphere. Outside of the furnace 22 the tube 32 passes into the sampling system 20. A quench box such as a water jacket or other means for providing rapid cooling preferably surrounds a portion of the sample tube 32 within the sampling system 20 and is operable to quench the sample of gas soon after it is withdrawn from the furnace. This quenching terminates any reactions in the sample and provides assurance that the composition of the sample gas remains substantially the same as that of the atmosphere within the carburizing chamber 34. The sampling system 20 also preferably includes a filter for removing particulates from a sample directed therethrough.

Measurement of the partial pressures of carbon monoxide gas and carbon dioxide gas in a sample is accomplished in a multi-component analyzer 24 which is connected to the sampling system 20 by means of a sample line 40. A gas inlet line 42 extending into the analyzer 24 receives the quenched and filtered sample from the sample line 40, and a gas outlet line 44 permits discharge of the sample after its passage through the analyzer 24. Within the general scope of the invention, the analyzer may be any apparatus capable of determining the content of carbon monoxide and of carbon dioxide in a sample of furnace gas. For example, a mass spectrometer or gas chromatograph may be suitable as an analyzer. However, an infrared analyzer such as that shown in FIG. 4 is currently preferred over all other analyzers because of its relative simplicity, fast response, and ability to provide continuous analysis of the atmosphere of a heat-processing furnace.

The infrared analyzer 24 of the invention utilizes the known principle that the degree of absorption by a gas of an infrared signal of selected wavelength which is directed through the gas is a function of the concentration of particular components in the gas. Thus the preferred analyzer 24 shown in FIG. 4 includes a sample flow cell 46 through which furnace gases may flow and an optical system 48 for generating radiation signals and directing the signals through the flow cell 46. Both the cell 46 and the optical system 48 are housed within a box 50 which is substantially gas tight.

The flow cell 46 of the infrared analyzer 24 comprises a gas tight shell 52 with optically transparent windows 54 and 56 at opposite ends thereof. The shell 52 also has an inlet port 58 in fluid communication with the gas inlet line 42 for continuously admitting a gas sample into the flow cell 46 and an outlet port 60 in fluid communication with the gas outlet line 44 for continuously discharging a gas sample from the flow cell 46. Since the absorption of infrared radiation by the gas within the cell 46 is a strong function of the gas pressure, pressure regulators 62 and 64 may also be included within the inlet line 42 and the outlet line 44 respectively to keep pressure within the flow cell and flow through the cell at constant desired values. If pressure within the cell 46 is held constant, then, as explained hereinafter, corrections must be made to the absorption measurement for various gaseous components of the sample to obtain the absolute values of partial pressure required in the calculation of carbon potential.

The optical system 48 of the infrared analyzer 24 includes a radiant energy source 66 and a set of optical filters such as the narrow bandpass optical filters 68, 70, and 72 each of which is operable to pass a selected narrow band of infrared radiation defined by a wavelength of interest. The filters 68, 70 and 72 typically are chosen to have half-power bandwidths of 0.1 to 0.2 microns. For one of the filters, e.g., the filter 68, a suitable wavelength of interest may be 4.27 microns, a wavelength at which energy is strongly absorbed by carbon dioxide gas but not by other components of the gas which could interfere with detection of carbon dioxide. A wavelength of 4.76 microns may be used for the filter 70 since at this wavelength energy is strongly absorbed by carbon monoxide gas but not by other components. A wavelength of 4.08 microns is suitable for the filter 72 since energy at this wavelength is absorbed weakly, if at all, by the gases normally present in a furnace atmosphere, and hence the band of radiation passed by the filter 72 is usable as a reference signal. The filters 68, 70, and 72 are mounted in a positioning mechanism 74 which permits each of the filters to alternately be moved into a position intercepting a beam of radiant energy from the source 66.

Additional optical filters such as the filters 75 and 76 shown in dashed form in FIG. 4 may be included in the analyzer 24 to pass infrared radiation at wavelengths at which energyy is strongly absorbed by gases such as methane and water vapor to permit detection of these gaseous constituents. Measurement of methane may be used in connection with an alarm (not shown) which is triggered if methane levels become excessive. The measurement of water vapor may be used for determining carbon activity according to an embodiment of the invention which is described more fully below.

Also included in the optical system 48 is a focusing mirror 78 for directing a beam of radiant energy from the source 66 through a selected one of the filters such as the filter 70 as shown in FIG. 4, and a focusing mirror 79 for directing the beam of infrared radiation passed by the selected filter through the flow cell 46. A third focusing mirror 80 is positioned downstream of the flow cell 46 in line with the transparent window 56 for directing the beam of radiation transmitted through the cell 46 to a radiation detector 82 which converts radiation intensities to electrical signals and transmits them to the processor 26. One detector suitable for use in the infrared analyzer 24 is a pyroelectric detector sold by Barnes Engineering Company of Stamford, Connecticut and which includes a deuterated triglycine sulfate (DTGS) detecting element. Since this preferred pyroelectric detector 82 is an AC (alternating current) device, the optical system 48 of the infrared analyzer 24 also includes a tuning fork shutter 84 preferably located between the focusing mirror 79 and the group of filters 68, 70, and 72. The shutter 84 operates as a beam chopper to interrupt the beam of radiant energy from the source 66 and to produce a nearly sinusoidal radiation signal which retains its AC nature in passing through the selected filter and the sample cell 46 and thus is compatible with the pyroelectric detector 82.

To assure environmental stability, one or more heaters (not shown) may be included in the infrared analyzer 24 for controlling the temperature of the flow cell 47 and of optical components such as the optical filters. Preferably a dry gas supply 86 is also provided as indicated in FIG. 4 fur purging water vapor and other gases such as carbon dioxide from the air within the box 50 housing the otptical system 48 and the flow cell 46. Purging is desirable since the presence of even relatively low levels of water vapor and carbon dioxide in the optical path outside the flow cell 46 can interfere with the measurement of the gaseous components of the sample flowing through the cell 46. The purge gas may be dry air and, if so, a preferred gas supply 86 comprises a compressor and a regenerative, molecular sieve-type drier. The dry gas supply 86 furnishes air to the interior of the box 50 by means of an inlet line 88 extending between the gas supply 84 and an inlet port 90. An outlet port 92 in the box 50 at a suitable location remote from the inlet port 90 permits the outflow of purged gases from the analyzer 24.

The output of the analyzer 24 is an AC electrical signal from the radiation detector 82 whose amplitude is a function of the particular optical filter which is in position and of the composition of the sample gas flowing through the flow cell 46. When, for example, the filters 68, 70, and 72 are moved successively into position by means of the positioning mechanism 74, three analyzer output signals are successively produced which may be termed a $CO_2$-absorbed, a CO-absorbed, and a reference signal. These analyzer output signals are directed to the processor 26 along an electrical line 94. A temperature signal from the thermocouple 28 is also applied to the processor 26 as an input along a line 96 (FIG. 3). The processor 26, which preferably includes a microprocessor for digital processing of signals, forms ratios of the $CO_2$-absorbed and CO-absorbed signals to the reference signal. Mole fractions of $CO_2$ and CO are determined in the processor 26 by fitting these ratios to curves developed from prior analysis of gases with known mole fractions of CO and $CO_2$. Absolute partial pressures of $CO_2$ and CO are then computed from the mole fractions of $CO_2$ and CO and a correction factor derived from measured atmospheric pressure—for example by means of a pressure transducer 97 (see dashed lines in FIG. 3). A line 98 permits input of the atmospheric pressure signal to the processor 26. Using the thus-determined partial pressures and the measured furnace temperature, in conjunction with equations (6), (8), (10), and (11) set forth above, the processor 26 determines the carbon potential of the atmosphere within the furnace 22. The values of carbon potential may be calculated at selected time intervals or substantially continuously by the processor 26. These values form a carbon potential signal which may be directed as output from the processor 26 to a digital display 99 along a line 100. The carbon potential signal is also converted by the processor 26 to an analog signal and directed along a line 102 to the atmosphere control 30 and, optionally, to a strip chart recorder 104 along a line 106.

The atmosphere control 30 includes means for adjusting the flow of a control agent such as natural gas which passes to the furnace 22 along an inlet line 108 to produce desired levels of carbon potential in the furnace atmosphere. The adjustment means may be an on-off or proportional controller or any other suitable flow control. Also provided either as part of the control 30 or the processor 26 are means for comparing the carbon potential signal calculated by the processor 26 with a predetermined desired value of carbon potential so that the difference therebetween may be minimized through appropriate operation of the control 30. If the comparison means is part of the processor 26, then the signal directed to the atmosphere control 30 along the line 102 is a control signal rather than the analog value of carbon potential calculated by the processor 26.

In FIG. 3, there is shown in dashed form an oxygen probe 110 and an electrical line 112 which form part of an alternate embodiment of the invention. As is explained below, this embodiment permits the determination of carbon content of a part surface by measurement of the $O_2$ and CO content of the furnace atmosphere rather than the $CO_2$ and CO content.

As a basis for determining the activity of carbon at the part surface by measurement of $O_2$ and CO, consider the following reaction which expresses the equilibrium established in the furnace atmosphere between CO, $CO_2$, and $O_2$:

  (12)

The combination of reactions (2) and (12) yields the reaction

  (13)

whose equilibrium relationship is $$a_{g13} = (P_{CO})(K_{13})/(P_{O_2})^{\frac{1}{2}}$$  (14)

Hence the activity of carbon at the part surface may be determined from equations (8) and (14), measured values of temperature (for calculating $K_{13}$) and measured values of the partial pressures of CO and $O_2$. The partial pressure of CO for a representative sample of the furnace atmosphere may be measured by operating the infrared analyzer 24 in the manner described above wherein a CO-absorbed signal and a reference signal are produced and then combined in the processor 26. The partial pressure of $O_2$ may be determined from the oxygen probe 110 which projects into the chamber 34 of the furnace 22. The oxygen probe 110 is preferably a solid electrolyte concentration cell for generating an oxygen potential signal indicative of the partial pressure of oxygen of the furnace atmosphere. This oxygen potential signal is transmitted along the line 112 to the processor 26 for determination of the partial pressure of $O_2$. The processor then calculates the activity of carbon at the part surface ($a_s$) from the partial pressures of $O_2$ and CO. Carbon content of the part surface may then be computed in the processor 26 by substituting the calculated values of $a_s$ and a temperature signal from the thermocouple 28 into equations (10) and (11).

The oxygen probe 110, when used in combination with an infrared analyzer 24 which includes the filters 70 and 76 for measuring the carbon monoxide and water vapor content of a sample, permits determination of the carbon content of a part surface using the equilibrium relationship (7) for reaction (3). This is possible because once the oxygen content is measured by means of the oxygen probe 110 and the water vapor content is measured by means of the infrared analyzer 24, the hydrogen content (and hence the partial pressure of $H_2$) may be determined by balancing the equilibrium reaction:

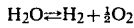  (15)

Once the $H_2$ content and the partial pressure of $H_2$ are computed in the processor 26, the partial pressure of $H_2$ may be substituted into equation (7) along with the partial pressures of $H_2O$ and CO derived from signals from the infrared analyzer 24. Carbon activity at the part surface may thus be calculated from these three parameters plus temperature data. Carbon content can then be obtained using equations (10) and (11).

Operation of the preferred apparatus for monitoring and controlling carbon potential of the atmosphere within the carburizing furnace 22 will now be briefly reviewed. A gas sample is withdrawn from within the furnace 22 through the sample tube 32. After the sample is quenched and particulates are removed from the sample during its passage through the sampling system 20, the sample gas is passed through the flow cell 46 within the analyzer 24 and is exhausted through the gas outlet line 44. While the sample gas is passing continuously through the flow cell 46, a set of three narrow band infrared radiation signals produced by the radiant energy source 66, tuning fork shutter 84, and filter 68, 70, and 72 in the analyzer 24 are directed in a predetermined sequence through the flow cell 46. These signals, whose wavelengths are determined by the movable filters 68, 70, and 72, are selected to comprise one signal which is strongly absorbed by $CO_2$ gas, one signal which is strongly absorbed by CO gas, and a reference signal not absorbed to any great degree by $CO_2$, CO or other gases normally present in a carburizing atmosphere. A pyroelectric detector 82 senses the unabsorbed radiation signals which emerge from the downstream end of the flow cell 46 and converts them to electrical output signals of the analyzer 24. The analyzer output signals are transmitted to the processor 26 along with a temperature signal from the thermocouple 28. From these signals and absorption-concentration data for gases of known composition, the processor 26 computes the concentration, and then the partial pressures, of $CO_2$ and CO gas present in the sample from the furnace atmosphere. From the partial pressures, the processor 26 calculates carbon activity according to equations (6) and (8) set forth above, then determines carbon potential of the furnace atmosphere using equations (10) and (11). The thus-determined carbon potential is used for adjusting the flow of a control agent such as natural gas supplied to the furnace 22 through the control 30 to minimize the difference between the carbon potential desired for optimum carburization of parts and the value of carbon potential determined by the monitoring and control system of the invention. Thus the carbon potential may be accurately controlled and only the proper amount of natural gas need be used.

FIGS. 5–8 show results of carburizing tests conducted to check the ability of the preferred apparatus of the invention to accurately determine the carbon potential of a furnace atmosphere. The tests were performed on one inch diameter SAE 1020 steel bars in an industrial batch furnace. An AGA (American Gas Association) Class 501 carrier gas, with natural gas as the enriching or control agent, was used as the furnace atmosphere in all the tests except for those whose results are summarized in FIG. 7 wherein a non-conventional atmosphere was substituted for the Class 501 carrier gas. After the test bars were carburized, the surface layers of the bars were removed by machining and the machined chips accurately analyzed for carbon content according to well known procedures. The curves of FIGS. 5–8 show the resulting carbon content of the analyzed bars as percent carbon by weight plotted versus distance from the surface of the bar. The hatched symbols are values of carbon potential determined by the apparatus of the invention during the test using measurements of the partial pressures of carbon dioxide and carbon monoxide in a sample and of the temperature of the furnace atmosphere. The band or height of each symbol does not represent the error limits of the apparatus, but indicates the variation in carbon potential which occurred and was recorded by the apparatus during the total period of each carburizing test.

Figure 5:
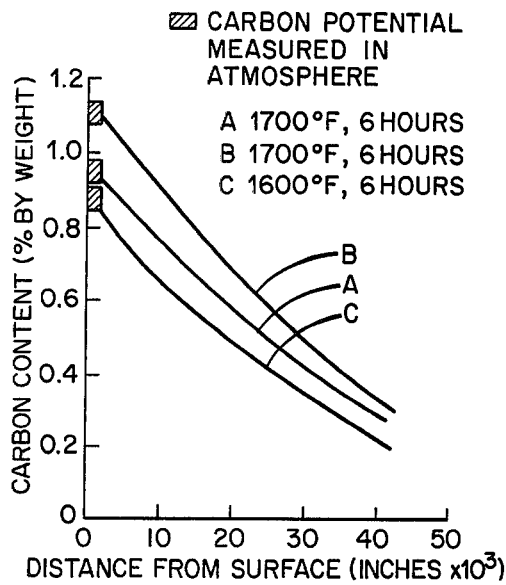
FIGS. 5-8 are graphs showing the carbon content versus depth of carburized specimens, and the values of carbon potential or carbon content of these specimens as determined according to a preferred embodiment of the invention.
Figure 6:
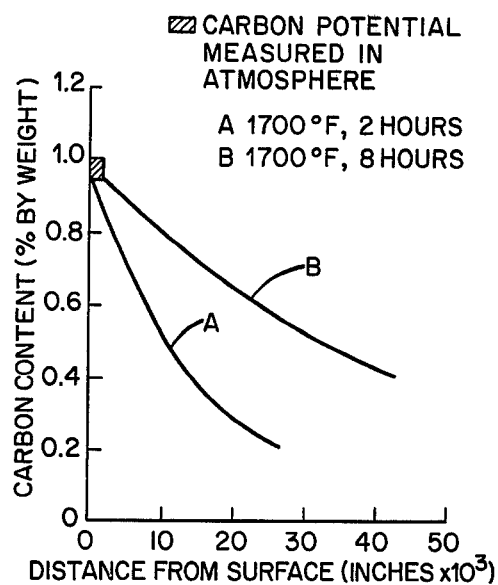

FIG. 5 shows results of tests for different carbon levels produced by varying the carburization temperature (Curves B and C) and by varying the natural gas enrichment (curves A and B). The results indicate excellent agreement between the surface carbon potential determined by the monitoring and control system of the invention and the carbon content measured by direct post-carburization analysis of the steel of the test bars. A similar level of agreement is indicated in FIG. 6, whose test results demonstrate the ability of the apparatus to accurately monitor carbon potential over varying intervals of time.

Figure 7:
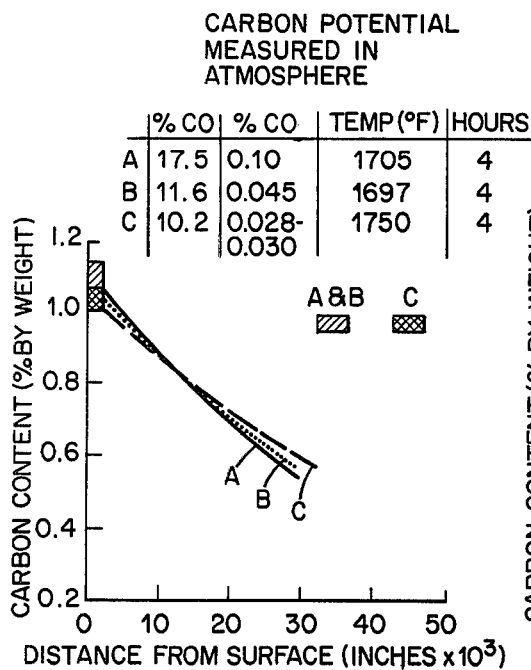

In FIG. 7 there are shown results of tests in which test bars were carburized in non-conventional furnace atmospheres selected to check the ability of the apparatus of the invention to monitor and control carbon potential when large deviations occur in the composition of a furnace atmosphere. Such deviations may occur, for example, as a result of intentional addition of ammonia for carbonitriding or of nitrogen for dilution to reduce natural gas consumption. They may also result from unintentional factors such as high air leaks. Curves A and B in FIG. 7 are carbon gradients for tests wherein the standard AGA Class 501 carrier gas was diluted with 40 to 50 percent of nitrogen. Curve C reflects results from a test wherein the furnace atmosphere included very low CO and $CO_2$ contents. For all three tests excellent agreement is again indicated between the surface carbon content determined by the monitoring and control system and the values found by post-carburization analysis.

Figure 8:
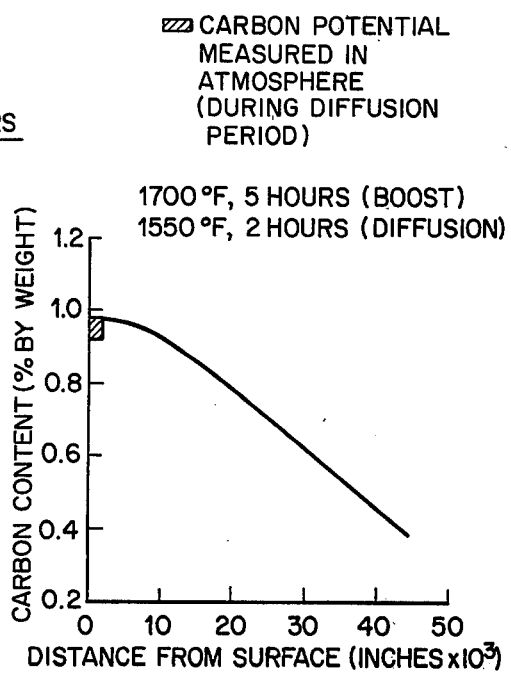

FIG. 8 shows a carbon gradient established during a "boost-diffusion" test similar to that used in the heat-processing industry for deep case carburizing. In this test a furnace atmosphere of high carbon potential was first provided to cause transfer of a large amount of carbon to the steel bar, then the temperature and carbon potential of the atmosphere were reduced to achieve a desired overall carbon gradient. As in all the tests discussed above, the values of surface carbon potential determined by the apparatus of the invention correspond closely to the actual values measured after machining surface layers from the test specimens.

Thus there has been described an apparatus for accurately monitoring and controlling the amount of carbon transferred to the surface of parts by a heat-processing furnace. The apparatus has been shown to precisely and reliably determine carbon potential in a carburizing furnace during operation with atmospheres of widely differing compositions and with different carburization times and temperatures.

While the invention has been shown and described with reference to preferred embodiments thereof, it will be apparent that various changes may be made without departing from the scope and spirit of the invention, and thus other embodiments are within the following claims.

What is claimed is:

1. Apparatus for monitoring and control of the carbon potential in the atmosphere of a heat processing furnace comprising:

means for measuring the temperature of said atmosphere and for producing a temperature signal;

sampling means for withdrawing from the furnace a sample of said atmosphere;

an infrared analyzer connected to said sampling means outside of said furnace for receiving and analyzing said sample; said analyzer including means for producing a $CO_2$-absorbed electrical signal indicative of the partial pressure of carbon dioxide of said sample and a CO-absorbed electrical signal indicative of the partial pressure of carbon monoxide of said sample;

a microprocessor electrically connected to said infrared analyzer and to said temperature measuring means, said microprocessor operable to calculate a carbon potential signal from said temperature signal and said $CO_2$-absorbed and CO-absorbed electrical signals; and control means for comparing said calculated carbon potential signal with a predetermined desired value of carbon potential and adjusting the flow of a control agent to said furnace to minimize the difference between said desired value and said carbon potential signal calculated by said microprocessor.

2. Apparatus as in claim 1, wherein said infrared analyzer comprises:

a sample flow cell;

means for continuously directing said sample through said flow cell;

an optical system for producing a first infrared radiation signal in a narrow bandwidth including a wavelength at which radiant energy is strongly absorbed by carbon dioxide gas, for producing a second infrared radiation signal in a narrow bandwidth including a wavelength at which radiant energy is strongly absorbed by carbon monoxide gas, for producing a third infrared signal in a narrow bandwidth at which substantially no radiation is absorbed by carbon dioxide gas or carbon monoxide gas, and for directing each of said infrared radiation signals in a predetermined sequence through said sample flow cell; and means for detecting the amount of radiation transmitted through said sample and for producing said $CO_2$-absorbed signal, said CO-absorbed signal, and a reference signal when said first, second, and third infrared signals are, respectively, directed through said flow cell;

said infrared analyzer and said microprocessor providing continuous analysis of sample gases to permit continuous monitoring and control of the carbon potential in the atmosphere of said furnace.

3. Apparatus as in claim 1 wherein said control means comprises an atmosphere controller for regulating the flow of natural gas to said heat-processing furnace.

* * * * *